United States Patent [19]

Lui et al.

[11] Patent Number: 6,021,344

[45] Date of Patent: Feb. 1, 2000

[54] FLUORESCENCE SCOPE SYSTEM FOR DERMATOLOGIC DIAGNOSIS

[75] Inventors: Harvey Lui, Vancouver; Haishan Zeng, Delta; Calum E. MacAulay, Vancouver; Branko Palcic, Vancouver; David I. McLean, Vancouver, all of Canada

[73] Assignee: Derma Technologies, Inc., Vancouver, Canada

[21] Appl. No.: 08/984,391

[22] Filed: Dec. 3, 1997

[30] Foreign Application Priority Data

Dec. 4, 1996 [CA] Canada ................................ 2192036

[51] Int. Cl.⁷ ........................................................ A61B 5/00
[52] U.S. Cl. ............................ 600/476; 600/473; 351/165
[58] Field of Search .................................... 600/476, 473, 600/475, 477, 478, 310, 317; 351/163, 165

[56] References Cited

U.S. PATENT DOCUMENTS

| | | | |
|---|---|---|---|
| 3,995,937 | 12/1976 | Baues et al. ............................... | 350/96 |
| 4,045,125 | 8/1977 | Farges ....................................... | 350/166 |
| 4,134,644 | 1/1979 | Marks et al. . | |
| 4,151,411 | 4/1979 | Derderian et al. ....................... | 250/225 |
| 4,376,889 | 3/1983 | Swift ......................................... | 250/213 |
| 4,511,222 | 4/1985 | Biren ........................................ | 350/441 |
| 4,595,262 | 6/1986 | Ogle .......................................... | 350/404 |
| 4,718,417 | 1/1988 | Kittrell et al. .......................... | 128/303.1 |
| 4,744,633 | 5/1988 | Sheiman ................................... | 350/132 |
| 4,893,898 | 1/1990 | Beard ........................................ | 350/132 |

(List continued on next page.)

FOREIGN PATENT DOCUMENTS

| | | | |
|---|---|---|---|
| 0113152 | 7/1984 | European Pat. Off. ........... | A61B 5/00 |
| 0783867 | 7/1997 | European Pat. Off. ........ | A61B 5/103 |
| WO 94/16622 | 8/1994 | WIPO .............................. | A61B 6/00 |
| WO 96/08201 | 3/1996 | WIPO .............................. | A61B 5/103 |
| WO 96/36273 | 11/1996 | WIPO .............................. | A61B 5/00 |
| WO 96/39925 | 12/1996 | WIPO .............................. | A61B 5/00 |

OTHER PUBLICATIONS

Bissonnette et al., Detection of Autofluorescence Due to Protoporphyrin IX in the Stratum Corneum of Psoriasis Plaques. Abstract MPM–F10. *Photochemistry and Photobiology* 65(S):49S, 1997.

Cascinelli et al., A possible new tool for clinical diagnosis of melanoma: The computer. *Journal of the American Academy of Dermatology*, 16:361–367, 1987.

Kini and Dhawan, Three–Dimensional Imaging and Reconstruction of Skin Lesions. *Computerized Medical Imaging and Graphics*, 16:153–161, 1992.

Dhawan and Sicsu, Segmentation of Images of Skin Lesions Using Color and Texture Information of Surface Pigmentation. *Computerized Medical Imaging Graphics*, 16:163–177, 1992.

(List continued on next page.)

*Primary Examiner*—William E. Kamm
*Assistant Examiner*—Shawna J Shaw
*Attorney, Agent, or Firm*—Joshua King

[57] ABSTRACT

Apparatus for the diagnosis of a skin disease site by visual fluorescence inspection comprising an excitation light source for illuminating the disease site, a light guide for transmitting the excitation light directly to the disease site to generate fluorescence light and viewing goggles for processing the excitation light reflected and the fluorescence light emitted from the disease site to provide a fluorescence image of the disease site to a user. The fluorescence image is used to aid the medical assessment of skin conditions and the diagnosis of cutaneous diseases by supplementing the visual assessment of skin lesions made by the naked eye. The apparatus can be used in several modes of operation that permit the viewing of full color fluorescence images and enhanced two color images. The apparatus can also use image intensifying equipment to amplify fluorescence light so that even very weak fluorescing objects can be seen. A method for acquiring and viewing the fluorescence images is also disclosed.

35 Claims, 3 Drawing Sheets

U.S. PATENT DOCUMENTS

| | | | |
|---|---|---|---|
| 4,894,547 | 1/1990 | Leffell et al. | 250/461.2 |
| 4,927,222 | 5/1990 | Kamiya et al. | 350/96.15 |
| 4,957,114 | 9/1990 | Zeng et al. | 128/665 |
| 5,028,594 | 7/1991 | Carson | 514/23 |
| 5,144,344 | 9/1992 | Takahashi et al. | 351/44 |
| 5,170,501 | 12/1992 | White . | |
| 5,177,509 | 1/1993 | Johansen et al. | 351/44 |
| 5,184,156 | 2/1993 | Black et al. | 351/158 |
| 5,304,173 | 4/1994 | Kittrell et al. | 606/15 |
| 5,450,857 | 9/1995 | Garfield et al. | 128/778 |
| 5,452,723 | 9/1995 | Wu et al. | 128/664 |
| 5,456,260 | 10/1995 | Kollias et al. | 128/665 |
| 5,467,767 | 11/1995 | Alfano et al. | 128/665 |
| 5,507,287 | 4/1996 | Palcic et al. | 128/633 |
| 5,556,612 | 9/1996 | Anderson et al. | 424/59 |
| 5,582,168 | 12/1996 | Samuels et al. | 128/633 |
| 5,590,660 | 1/1997 | MacAulay et al. | 128/664 |
| 5,592,245 | 1/1997 | Moore et al. . | |
| 5,594,843 | 1/1997 | O'Neill | 395/127 |
| 5,612,540 | 3/1997 | Richards-Kortum et al. | 250/461.2 |
| 5,628,310 | 5/1997 | Rao et al. | 128/633 |
| 5,647,368 | 7/1997 | Zeng et al. | 128/665 |
| 5,687,730 | 11/1997 | Doiron et al. | 128/665 |
| 5,708,490 | 1/1998 | Wieczorek | 351/47 |

OTHER PUBLICATIONS

Di Carlo, Thermography and the Possibilities for Its Applications in Clinical and Experimental Dermatology, *Clinics in Dermatology*, 13:329–336, 1995.

Feld et al., Detection and characterization of human tissue lesions with near infrared Raman spectroscopy. *SPIE Proceedings*, 2388:99–104, 1995.

Green et al., Computer image analysis of pigmented skin lesions. *Melanoma Research*, 1:231–236, 1991.

Herbin et al., Color Quantitation Through Image Processing in Dermatology. *IEEE Transactions on Medical Imaging*, 9:262–269, 1990.

Jimbow et al., Melanin Pigments and Melanosomal Proteins as Differentiation Markers Unique to Normal and Neoplastic Melanocytes. *Journal of Investigative Dermatology*, 100:259S–268S, 1993.

Liu et al., Raman, fluorescence, and time–resolved light scattering as optical diagnostic techniques to separate diseased and normal biomedical media. *Journal of Photochemistry and Photobiology B: Biology*, 16:187–209, 1992.

Lui et al., Optical Spectroscopy as a Potential Diagnostic Aid for Dermatology. Clinical Dermatology 2000—An International Congress, Vancouver, BC, May 28–31, 1996, Programme and Abstracts, Abstract 584, p. 176.

Lui et al., Ratio Analysis of Reflectance and Fluorescence Spectra of Diseased Skin. 24$^{th}$ Annual Meeting of the American Society of Photobiology, Atlanta, Georgia, Jun. 15–20, 1996.

Owen et al., New spectroscopic instrument based on volume holographic optical elements. *SPIE Proceedings*, 2406:260–267, 1995.

Seidenari, High–Frequency Sonography Combined with Image Analysis: A noninvasive Objective Method for Skin Evaluation and Description. *Clinics in Dermatology*, 13:349–359, 1995.

Stoecker and Moss, Editorial: Digital Imaging in Dermatology. *Computerized Medical Imaging and Graphics*, 16:145–150, 1992.

Stoecker et al., Texture in Skin Images: Comparison of Three Methods to Determine Smoothness. *Computerized Medical Imaging and Graphics*, 16:179–190, 1992.

Umbaugh et al., Automatic Color Segmentation Algorithms. *IEEE Engineering in Medicine and Biology*, 75–82, 1993.

Zeng, Human Skin Optical Properties and Autofluorescence Decay Dynamics. Ph.D. Thesis, The University of British Columbia, Vancouver, Canada, 1993.

Zeng et al., A computerized autofluroescence and diffuse reflectance spectroanalyser system for in vivo skin studies. *Physics in Medicine and Biology*, 38:231–240, 1993.

Zeng et al., Autofluorescence distribution in skin tissue revealed by microspectrophotometer measurements. *SPIE Proceedings*, 1876:129–135, 1993.

Zeng et al., Novel Miscrospectrophotometer and its Biomedical Applications. *Optical Engineering*, 32:1809–1813, 1993.

Zeng et al., Laser–induced changes in autofluorescence of in vivo skin. *SPIE Proceedings*, 1882:278–290, 1993.

Zeng et al., Update on fluorescence spectroscopy studies of diseased skin. *SPIE Proceedings*, 2671E–42, 1993.

Zeng et al., Monte Carlo modeling of tissue autofluorescence measurement and imaging. *SPIE Proceedings*, 2135:94–104, 1994.

Zeng et al., Miniature spectrometer and multi–spectral imager as a potential diagnostic aid in dermatology. *SPIE Proceedings*, 2387:57–61, 1995.

Zeng et al., Miniature Spectrometer and Multi–Spectral Imager for Skin Diagnosis. Laser in Dermatology, Plastic Surgery and Burn Treatment at Biomedical Optics '95, San Jose, CA, Feb. 4–10, 1995, In: SPIE 2387–09:17, 1995.

Zeng et al., Spectroscopic and Microscopic Characteristics of Human Skin Autofluorescence Emission. *Photochemistry and Photobiology*, 61:639–645, 1995.

Zeng et al., Optical spectroscopy studies of diseased skin—preliminary results. *SPIE Proceedings*, 2628:281–285, 1995.

Zeng et al., Non–invasive, Bedside Autofluorescence Spectroscopy of Benign and Malignant Skin Lesions, abstract. Fourth Meeting of the Western Canadian Society for Clinical and Investigative Dermatology, Jasper, AB, Mar. 24–26, 1995.

Zeng et al., Optical spectroscopy studies of diseased skin, abstract. European BioMedical Optics—BIOS Europe '95, Barcelona, Spain, Sept. 12–16, 1995.

Zeng et al., Update on Fluroescence Spectroscopy Studies of Diseased Skin, abstract. SPIE BiOS'96, San Jose, CA, Jan. 27–Feb. 2, 1996, Paper 2671E–42, Session 8, p. 12.

Zeng et al., Quantative Analysis of Laser Induced Autofluorescence Spectra of Diseased Skin, abstract. Photonics China '96, Lasers in Medicine and Denistry: Diagnostics and Treatment, Beijing, China, Nov. 4–7, 1996.

Zeng et al., Reconstruction of in vivo skin autofluorescence spectrum from microscopic properties by Monte Carlo simulation. *Journal of Photochemistry and Photobiology B: Biology* 38: 234–240, 1997.

FLUORESCENCE SCOPE SYSTEM FOR DERMATOLOGIC DIAGNOSIS

CROSS REFERENCE TO RELATED APPLICATION

This application claims priority from Canadian Patent Application No. 2,192,036, filed Dec. 4, 1996, which application is hereby incorporated by reference in its entirety.

FIELD OF THE INVENTION

This invention relates to a method and apparatus for viewing fluorescence emissions from skin disease sites to assist in diagnosis of the site.

BACKGROUND OF THE INVENTION

Currently, the clinical diagnosis of skin disease is generally accomplished by visual inspection under white light illumination. In this process, the reflectance pattern of a skin lesion is examined. Visual diagnosis alone may not be particularly accurate for the early detection of skin cancer since many skin conditions have a similar appearance under white light. Therefore, when a suspect lesion is identified by visual examination, a biopsy is often performed for a definitive diagnosis. Not only is it crucial to diagnose skin pre-cancer or cancer at its early stage when it is curable, it is also important to improve the clinical diagnosis of suspect skin lesions so as to avoid unnecessary skin biopsies.

Several approaches have been tried to improve dermatologic diagnosis. Digital processing of reflectance images has been intensively investigated recently. Although reflectance imaging has led to improvements in registration, recording, and documentation of skin lesions, there has been little improvement in the diagnostic accuracy. The foregoing approach does not provide any additional data to the physician making the visual assessment because it is still based on the reflectance pattern of a lesion under white light illumination which is essentially the same pattern a human observer sees.

An alternative approach is ultraviolet UV or infrared IR photography which extends the visual perception of a physician to UV or IR reflectance patterns. However, the inconvenience due to delays in film image processing renders this technique impractical for everyday use.

A further alternative approach that is already in widespread medical use involves a "Wood's lamp" which consists of a mercury discharge lamp equipped with a filter that absorbs visible light, and transmits UVA light with a 365 nanometer peak. When using this device to assist in skin diagnosis, the eye serves as both the detector and the long pass filter. The eye is not sensitive to UV light, but is sensitive to visible fluorescent light. The "Wood's lamp" must be used in a darkened room, where the physician can see an image of a fluorescing disease site. The "Wood's lamp" is useful for the diagnosis of skin conditions such as tinea capitis, tinea versicolor erythrasma, and some pseudomonas infections, as well as aiding in the detection and diagnosis of hypopigmented lesions.

SUMMARY OF THE INVENTION

The apparatus and method of the present invention permit viewing of fluorescence emission images of skin to aid in the medical assessment of skin conditions and the diagnosis of cutaneous diseases by supplementing the visual assessment of skin lesions. Effectively, the apparatus and method of the present invention extend the vision of a physician to fluorescence images generated by any preselected UV wavelength light or visible wavelength light in order to assist in an accurate visual diagnosis.

Accordingly, the present invention provides apparatus for the diagnosis of a skin disease site by visual inspection comprising:

an excitation light source for illuminating the disease site;

means for transmitting the excitation light directly to the disease site to generate fluorescence light;

means for processing the excitation light reflected and the fluorescence light emitted from the disease site to provide a fluorescence image of the disease site to a user.

Using the apparatus of the present invention, both full color images and optically enhanced two color images over two specific wavelength bands of a fluorescing site can be viewed by a physician. An image intensifier version of the apparatus allows the physician to view even very weakly fluorescing sites.

In a further aspect, the present invention provides a method of diagnosing a skin disease site in low ambient light environment by visual inspection comprising the steps of:

illuminating the disease site with a preselected excitation light source to generate fluorescence light;

processing the excitation light reflected and the fluorescence light emitted from the disease site to generate processed fluorescence images; and viewing and evaluating the processed fluorescence images to permit visual diagnosis of the disease site.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

Figure 1:
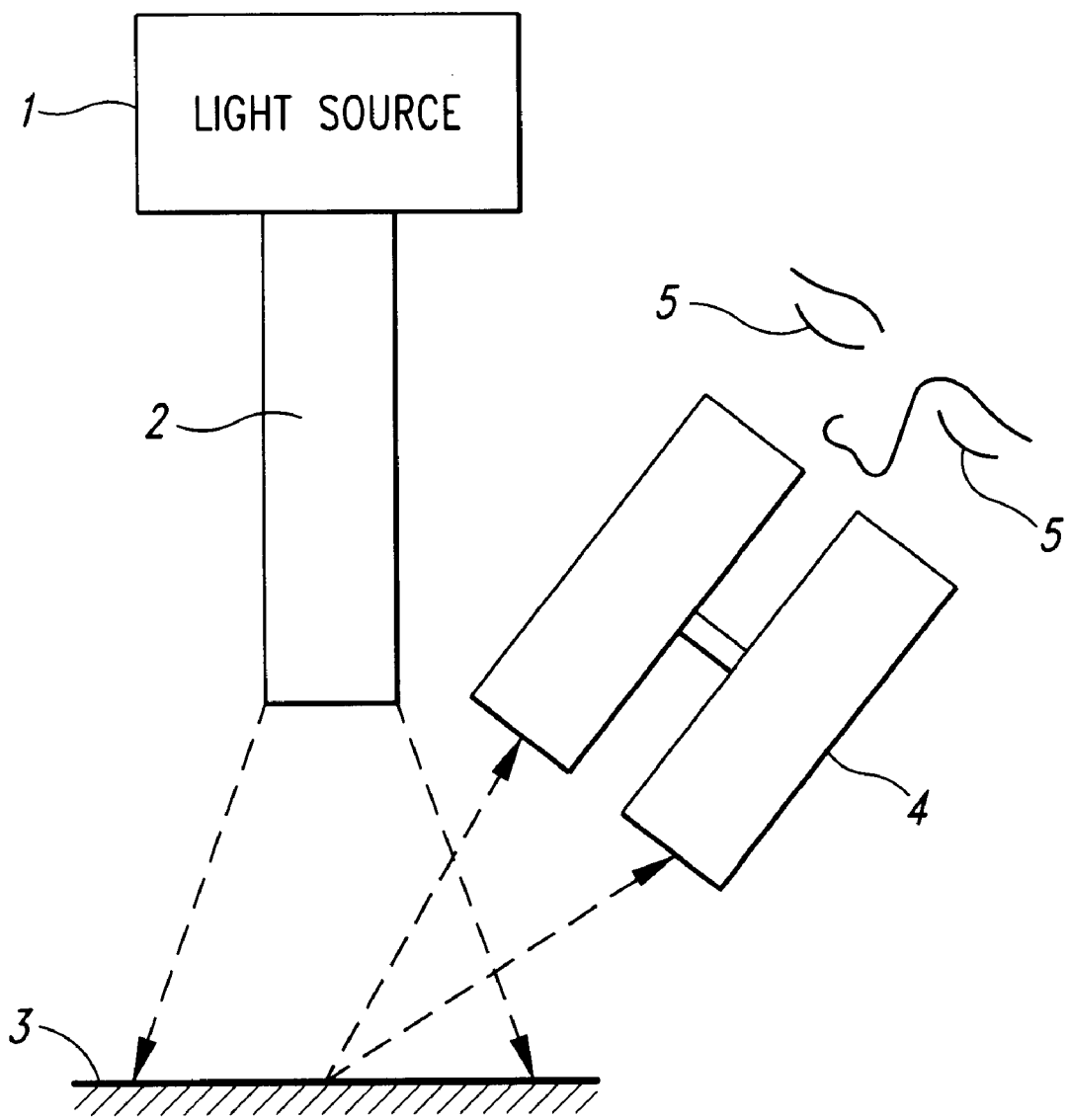
FIG. 1 is a schematic diagram showing an embodiment of the apparatus of the present invention.

Referring to FIG. 1, there is shown a schematic block diagram of a preferred embodiment of the apparatus of the present invention useful for dark room diagnosis of a skin disease site 3 by visual inspection. The apparatus includes an excitation light source 1 for illuminating disease site 3 and a light guide 2 for transmitting the excitation light directly to the disease site in order to generate fluorescence light. The apparatus also includes means for processing the reflected excitation light and the emitted fluorescence light from the disease site in the form of binocular viewing apparatus 4 adapted to be worn by a user such that fluorescence images are transmitted to the user's eyes 5. The foregoing apparatus is best operated under low ambient light conditions so as to minimize interference with the relatively weak fluorescence signals.

Light source 1 is selected to provide excitation light (either ultraviolet or visible light) for the disease site. The excitation light is conducted by light guide 2 to illuminate the skin at the disease site of a patient. Endogenous fluorophores such as tryptophan, collagen cross-links, collagen, elastin, NADH and others in the illuminated skin tissue are excited by the photons of the excitation light and emit fluorescence light. This fluorescence light is processed by the binocular viewing apparatus 4 for viewing by both eyes 5 of the user. The fluorescence emissions from the skin are very sensitive to the composition and structural changes of the tissue under examination. Different skin diseases or different prognostic stages of one lesion may show different composition and structural changes. Therefore, the cutaneous fluorescence emissions that the apparatus of the present invention permits to be observed provide more information about the skin under examination than would reflected light pattern is under white light. Thus, using the apparatus of the present application to perform fluorescence examination of the disease site in combination with conventional white light reflectance examination will permit better diagnostic accuracy.

Light source 1 is selected to provide excitation light that will generate tissue fluorescence. For example, a laser source such as a helium-cadmium (He—Cd) laser provides 442 nm blue light that generates fluorescence. Alternatively, a Mercury arc lamp light source can be used which provides UV and visible light at specific wavelengths, for example, a 365 nm UV line, a 405 nm blue line and a 436 nm blue line. Other types of lamp light sources may be used, such as a Wood's lamp, for illumination.

When a laser is used as a light source 1, light guide 2 is preferably an optic fiber. It has been determined that a fiber with a core diameter of about 400 $\mu$m and a micro lens attached at the fiber end adjacent the disease site works well as a light guide. Laser light is easily focused into the fiber and the microlens generates a uniform illumination spot. The diameter of the spot can be varied by changing the distance between the microlens tip and the skin surface.

If the light source is a Mercury arc lamp or other arc lamp such as a Xenon or metal halide arc lamp, an optic fiber bundle or liquid light guide of approximately 5 mm diameter is preferable as the light guide since it is impractical to focus light from an arc lamp into a single fiber. A 5 mm diameter fiber bundle or liquid light guide is adequate to capture sufficient light from the source for transmission to the disease site. A liquid light guide has better transmittance than a fiber bundle and thus more light is transmitted by a liquid light guide. However, this advantage is offset by the greater expense of the liquid light guide. The diameter of the light spot is varied in a similar manner as with the optic fiber by varying the distance between the end of the light guide and the skin surface.

Illumination may also be achieved without using a light guide. For example, LED (light emitting diode) panels and UV fluorescent lamps such as a Wood's lamp can be used to directly illuminate the skin.

Figure 2:
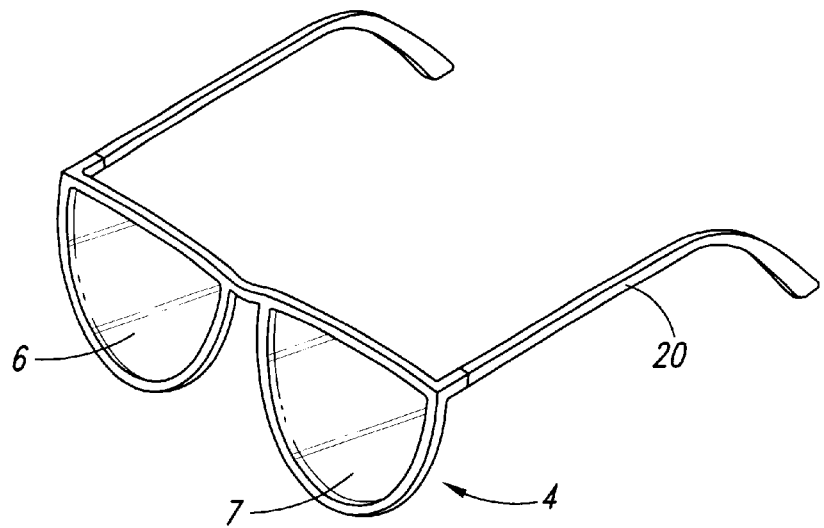
FIG. 2 is a detail view of an embodiment of the present invention that uses spectacles.

An example of a binocular viewing apparatus 4 is shown in FIG. 2 and comprises eye glass frames 20 with special light filters 6 and 7 mounted in either side of the frames to allow the transmission of an independent fluorescence image to each eye of the user. In an alternative arrangement, binocular viewing apparatus 4 comprises a set of goggles (not shown) to house light filters 6 and 7. The eye glass frames are preferably worn by users who do not normally wear eye glass, while the goggles arrangement can be worn over a user's conventional eye glasses.

There are a number of arrangements of light filters 6 and 7 in the apparatus of the present invention.

In a first embodiment, filters 6 and 7 are identical long pass filters selected to block the shorter wavelength excitation light and pass the longer wavelength emitted fluorescence light for viewing. In this manner, a full color fluorescence image of the disease site is transmitted to the user. By way of example, if a 442 nm He—Cd laser is used as light source 1 for fluorescence excitation, a 475 nm long pass filter (Scott glass GG475) can be used as filters 6 and 7.

In a second embodiment, filters 6 and 7 are selected to provide an enhanced two color image of the fluorescing disease site to the eyes of the user. Filters 6 and 7 are two different band pass filters, each filter being chosen to block the 'short wavelength excitation light and pass longer wavelength fluorescence light with set efficiencies for different wavelength bands to each eye. Therefore, each eye 5 sees an image of the fluorescing disease site in a color determined by the band pass filter in front of the particular eye. In addition to being different colors, the two images seen by the two eyes have different fluorescence intensity distributions. It has been determined experimentally that the brain of a user is able to compose the individual color images observed by each eye to form a single two color image of the fluorescing disease site that contains information in respect of the intensity variation and the color variation of the disease site as compared to the surrounding normal skin. The composed color at a particular location in the image is determined by the ratio of the integral fluorescence intensities over the two selected wavelength bands passed by filters 6 and 7. Therefore, the composed image perceived by the brain when using the apparatus of the present embodiment is a two dimensional distribution of the fluorescence intensity and the fluorescence ratio over two different wavelength bands. It is an enhanced two color image of the fluorescing disease which provides valuable information for skin disease diagnosis. Our studies have shown that the wavelength bands of filters 6 and 7 can be selected in response to fluorescence spectral studies of diseased skin to provide characteristic two color images that permit accurate diagnosis of a disease site condition.

In a third embodiment, filters 6 and 7 comprise two identical customised band pass filters, each filter being designed to block the excitation light and pass the emitted fluorescence light in at least two preselected wavelength bands. The two wavelength bands passed by filter 6 are identical to the two bands passed by filter 7 so that the viewing apparatus of the third embodiment permits the examination of two color enhanced fluorescence images as described above in relation to the second embodiment. The image perceived by the brain using the customised identical filters of the present embodiment is identical to the image perceived when using the two different band pass filters of the second embodiment.

Although the binocular viewing apparatus 4 of the second and third embodiments provide the same information regarding a disease site under examination, each embodiment has its own advantages and disadvantages. The different band pass filters 6 and 7 used in the second embodiment are easy to design and make. The disadvantage with using the two different band pass filters is that each eye is shown a different image and some training is necessary for a user to become comfortable with mentally combining the two different images. This is similar to the training that is necessary in order to view prepared photographs using special viewing glasses and be able to perceive a three dimensional image. In contrast, the disadvantage of using the same customised band pass filters in the third embodiment is that the filters are more difficult to design and manufacture and hence much more expensive. However, using a viewing apparatus fitted with the customised filters requires no special training as the same two color image is transmitted to each eye. Both eyes see both wavelength bands, and, therefore, the brightness of the perceived image will be approximately twice that perceived using the viewing apparatus of the second embodiment where each eye sees only one of the two wavelength bands.

Figure 3:
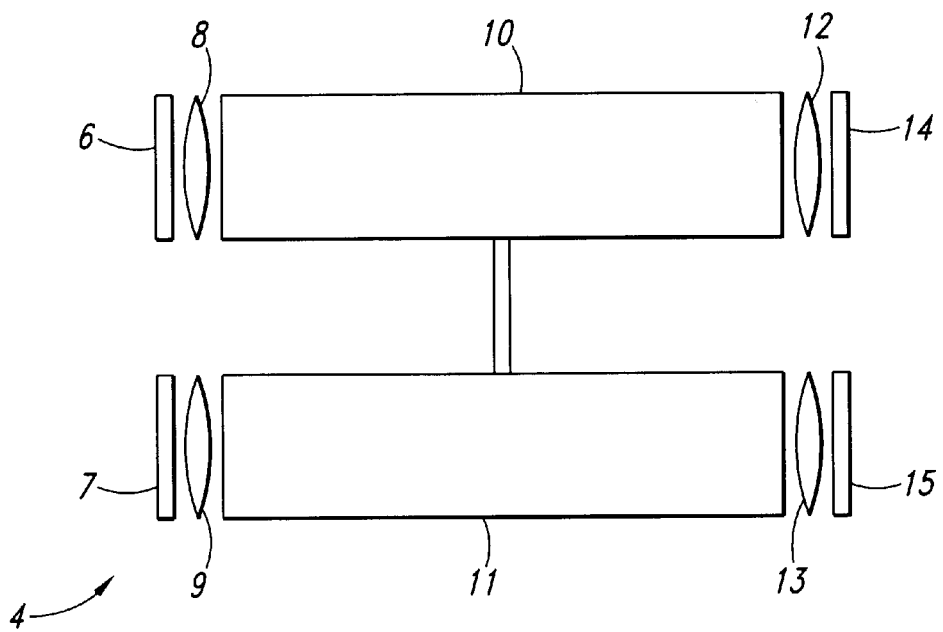
FIG. 3 is a detail view of an alternative embodiment that uses image intensifying means to enhance the fluorescence images transmitted to the user.

FIG. 3 is a schematic view of a further embodiment of the present invention involving another variation in the viewing apparatus 4. In this case, the viewing apparatus is provided with image intensifying means associated with the light filters comprising image intensifier 10 and 11. The principle of operation is the same as with the second embodiment of the viewing apparatus except that image intensifiers 10 and 11 are used to amplify the fluorescence light so that very faint fluorescing disease sites can be viewed.

The intensified viewing apparatus comprises a pair of tubular housings mounted in a binocular frame for presenting simultaneous images to each eye. Each tubular housing comprises a band pass filter 6 or 7, a first lens 8 or 9, an image intensifier 10 or 11, a second lens 12 or 13 and a final filter 14 or 15. Fluorescence light from the disease site is filtered by filters 6 or 7 which are preferably two different band pass filters. The filtered fluorescence light is then focused by lens 8 or 9 to form an image on the photocathode of the image intensifier 10 or 11. As is conventional, the photocathode converts photons into electrons. The number of electrons corresponding to each image pixel is then multiplied by a multi-channel microplate with high voltages at its two ends. The multiplied electrons exit from the microplate and collide with a phosphor screen to form an optical image again. Lens 12 or 13 focuses the images for transmittal to the eye. Filter 14 or 15 provides a means to adjust the color of the image presented to the eye. In combination with filter 14 or 15, different colored phosphors can be used in each of the phosphor screens of the image intensifiers 10 or 11 to create different colored images that are presented to each eye. In this manner, an optically enhanced two color image of the fluorescing disease site is presented to the two eyes of the user. As described previously, the two images are composed by the brain and perceived as a two dimensional distribution of the fluorescing intensity and the fluorescence ration over two different wavelength bands.

In association with the intensified viewing apparatus, light source 1 can be a pulsed source (flash lamp or pulsed laser), and intensifiers 10 and 11 can be gated to acquire images only when the skin is being exposed to the light pulses. An intense pulse light source with pulse width in the microsecond to nanosecond domain will generate cutaneous fluorescence that is much brighter than the ambient light. The image intensifiers are gated on during this period to acquire the fluorescence image. Outside of the pulse duration, the intensifiers are gated off, and the ambient reflected light images are not acquired. In this way, the cutaneous fluorescence images can be viewed with the ambient light on.

Figure 4:
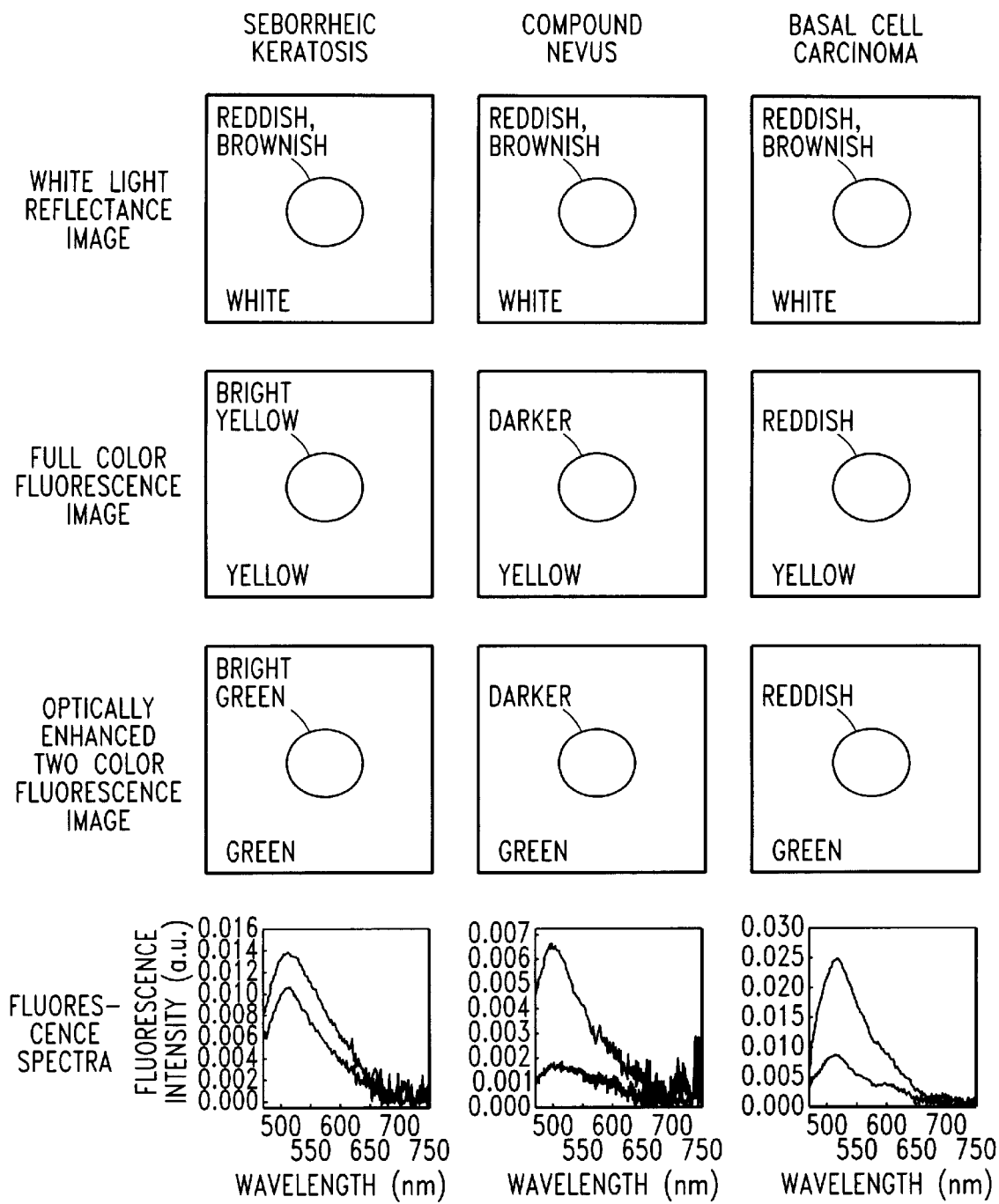
FIG. 4 is a table illustrating the visual appearance of three types of skin lesions when viewed under normal white light and using the apparatus and method of the present invention.

In order to demonstrate the use of the apparatus and method of the present invention, FIG. 4 is provided. FIG. 4 is a table showing in columns the visual appearance of three types of skin conditions, seborrheic keratosis, compound nevus and basal cell carcinoma, when viewed under different light. Each row of the table shows the skin conditions under a different light condition.

The first row is the reflectance images under white light of the three skin sites. These images show substantially what a physician sees with the naked eye. All three skin conditions can appear substantially the same: a reddish, brown area surrounded by generally white skin. Distinguishing between the various conditions is sometimes difficult.

Row 2 and 3 show the appearance of the skin lesions and their surrounding skin when view using 442 nm He—Cd laser excited fluorescence light. It is apparent that the coloring of the various lesions tends to be distinctive which greatly aids a user in differential diagnosis of the three different lesions.

Row 4 of FIG. 4 shows the fluorescence spectra, fluorescence wavelength plotted against fluorescence intensity, for the disease sites illuminated by the 442 nm He—Cd laser.

Row 2 contains full color fluorescence images of the sites using the apparatus of the first embodiment of the present invention where filters 6 and 7 are identical 475 nm long pass filters. The full color fluorescence images all have a yellowish background (normal skin). The seborrheic keratosis looks bright yellow since its spectrum has a higher intensity surrounding normal skin (see row 4). Both the compound nevus and bagel cell carcinoma look darker than the surrounding skin since their spectra have lower intensities than the surrounding skin. Therefore, the full color fluorescence images are useful for differentiating the seborrheic keratosis from the other two lesions.

In row 3, the images are optically enhanced two color images acquired using the apparatus of the second or third embodiments or the image intensified apparatus. In this particular example, the two wavelength bands selected are green (480 nm to 560 nm) and red (620 nm to 700 nm). The two color images have a greenish background identifying normal skin. The seborrheic keratosis looks bright green since its spectrum has higher intensities in the green band than surrounding normal skin. The transmittance of the two wavelength bands are selected so that the basal cell carcinoma looks reddish, the compound nevus looks dark grey and normal skin appears greenish. This is due to the fact that the ratio of the spectral maximum intensity of normal skin to that of the compound nevus is 4 while the ratio for basal cell carcinoma is 3.

The images of FIG. 4 are only a few examples of the differential diagnosis capabilities of the apparatus and method of the present invention which provide new information for skin diagnosis.

The present invention provides a number of important technical advantages that can be summarised as follows:

1. The apparatus of the present invention provides new information for skin diagnosis as compared to conventional white light examination.

2. In comparison to a Wood's lamp, different excitation wavelengths including visible light can be used for fluorescence examination. The enhanced two color fluorescence examination mode is a totally different mode than Wood's lamp, and it enhances the color ratio over two wavelength bands to provide more powerful discrimination capabilities.

3. The image intensified embodiment of the present invention allows very weak fluorescing disease sites to be view and diagnosed.

4. The apparatus of the present invention are relatively inexpensive and easy to use.

5. The apparatus and method of the present invention provides a new, non-invasive system for performing more accurate dermatologic diagnosis.

Although the present invention has been described in some detail by way of example for purposes of clarity and understanding, it will be apparent that certain changes and modifications may be practiced within the scope of the appended claims.

We claim:

1. A binocular viewing apparatus comprising a frame adapted to be worn on the head of a user, the frame comprising first and second light filters fixedly mounted on either side of the frame, the first filter positioned to transmit a first independent fluorescence image to a first eye of the user and the second filter positioned to transmit a second independent fluorescence image to a second eye of the user, wherein each filter blocks at least light having a wavelength of about 442 nm or less and each filter is a band pass filter that passes the fluorescence light in at least two different selected wavelength bands.

2. Apparatus as claimed in claim 1 in which the frame is an eyeglass frame.

3. Apparatus as claimed in claim 1 in which the frame is a goggle frame.

4. Apparatus as claimed in claim 1 in which the first and second light filters comprise two identical light filters.

5. Apparatus as claimed in claim 1 in which the at least one filter blocks light having a wavelength of less than about 475 nm.

6. Apparatus as claimed in claim 1 in which the at least two selected wavelength bands are green light and red light.

7. Apparatus as claimed in claim 6 in which the green light is from about 480 nm to about 560 nm and the red light is from about 620 nm to about 700 nm.

8. Apparatus as claimed in claim 1 in which the apparatus further comprises at least one image intensifier that intensifies the light passing through at least one of the first and second light filters.

9. Apparatus as claimed in claim 8 in which the apparatus further comprises at least two image intensifiers, one for each of the first and second light filters.

10. Apparatus as claimed 9 in which the first and second light filters comprise first and second band pass filters, the first band pass filter passing fluorescence light at a first wavelength band to the first image intensifier and the second band pass filter passing fluorescence light at a second wavelength band to the second image intensifier.

11. Apparatus as claimed in claim 10 further comprising an adjuster that adjusts the color of the fluorescence image transmitted to each eye.

12. Apparatus as claimed in claim 11 in which the adjuster comprises color filters located between the image intensifiers and the eyes of the user.

13. Apparatus as claimed in claim 1 in which the apparatus further comprises an excitation light source attached to the frame, the excitation light source able to induce fluorescence in human skin in front of the first and second light filters.

14. Apparatus as claimed in claim 13 in which the apparatus further comprises a light guide that transmits the excitation light from the excitation light source to the skin.

15. Apparatus as claimed in claim 14 in which the light guide comprises an optic fiber having a microlens on an end of the fiber located near the skin.

16. Apparatus as claimed in claim 15 in which the light guide comprises an optic fiber bundle.

17. Apparatus as claimed in claim 15 in which the light guide comprises a liquid light guide.

18. Apparatus as claimed in claim 13 in which the excitation light source comprises a laser light source.

19. Apparatus as claimed in claim 13 in which the excitation light source comprises an arc lamp selected from the group consisting of a Mercury arc lamp, a Xenon arc lamp, and a metal halide lamp.

20. Apparatus as claimed in claim 13 in which the excitation light source is selected from the group consisting of a LED panel and a fluorescent UV lamp for direct illumination of the skin.

21. Apparatus as claimed in claim 13 in which the apparatus further comprises at least one image intensifier that intensifies the light passing through at least one of the first and second light filters.

22. Apparatus as claimed in claim 21 in which the excitation light source comprises a pulsed light source and the at least one image intensifier acquires an image only when the pulsed light source is activated.

23. Apparatus for diagnosis of skin disease sites by visual fluorescence inspection comprising:

an excitation light source for providing excitation light for illuminating the disease site;

means for transmitting the excitation light directly to the disease site to generate fluorescence light; and means for processing the excitation light reflected and the fluorescence light emitted from the disease site to provide a fluorescence image of the disease site to a user, wherein the means for processing comprises first and second band pass filters, each filter blocking the excitation light and passing the fluorescence light in at least two different preselected wavelength bands, wherein each filter is arranged in either side of binocular frames to transmit an independent fluorescence image to each eye of the user.

24. Apparatus as claimed in claim 23 in which the binocular frames are eyeglass frames.

25. Apparatus as claimed in claim 23 in which the binocular frames are goggle frames.

26. Apparatus as claimed in claim 23 in which the two or more light filters comprise two identical light filters.

27. Apparatus as claimed in claim 23 in which the means for processing the light includes image intensifying means associated with the two or more light filters.

28. Apparatus as claimed in claim 27 further comprising an adjuster that adjusts the color of the fluorescence image transmitted to each eye.

29. Apparatus as claimed in claim 28 in which the adjuster comprises color filters located between the image intensifiers and the eyes of the user.

30. Apparatus as claimed in claim 23 in which the excitation light source comprises a pulsed light source and the image intensifying means acquires an image only when the pulsed light source is activated.

31. Apparatus as claimed in any one of claims 1, 2 or 23 in which the apparatus does not comprise an image intensifier.

32. A method of evaluating a potential human skin disease site by visual inspection comprising the steps of:

illuminating the disease site with a excitation light under conditions suitable and for a time sufficient to generate fluorescence light in the skin disease site;

passing the fluorescence light through at least one band pass light filter that passes the fluorescence light in at least two different selected wavelength bands, the at least one filter mounted in a binocular frame that is adapted to be disposed on the head of a user, the at least one filter blocking at least light having a wavelength of about 442 nm or less, thereby blocking the excitation light reflected from the disease site and transmitting the fluorescence light emitted from the disease site to at least one eye of the user to provide a transmitted fluorescence image; and viewing and evaluating the transmitted fluorescence image.

33. A method as claimed in claim 32 in which the at least two different wavelength bands are green light and red light.

34. A method as claimed in claim 33 in which the green light is from about 480 nm to about 560 nm and the red light is from about 620 nm to about 700 nm.

35. A method as claimed in claim 32 in which the method does not comprise passing the image that is transmitted to the eyes of the user through an image intensifier.

* * * * *